United States Patent [19]

Stewart et al.

[11] Patent Number: 5,648,336

[45] Date of Patent: Jul. 15, 1997

[54] BRADYKININ ANTAGONIST PEPTIDES CONTAINING INDANE-SUBSTITUTED AMINO ACIDS

[75] Inventors: John M. Stewart; Lajos Gera, both of Denver; Eric T. Whalley, Golden, all of Colo.

[73] Assignee: University of Colorado, Boulder, Colo.

[21] Appl. No.: 344,636

[22] Filed: Nov. 18, 1994

[51] Int. Cl.$^6$ .................. A61K 38/00; C07K 7/06; C07K 14/00
[52] U.S. Cl. .................. 514/15; 530/327; 530/328; 530/326; 530/314; 514/13
[58] Field of Search ................ 514/15; 530/327–328, 530/314, 326

[56] References Cited

U.S. PATENT DOCUMENTS

| 4,693,993 | 9/1987 | Stewart et al. | 530/314 |
| 4,923,963 | 5/1990 | Stewart et al. | 530/314 |
| 5,416,191 | 5/1995 | Cheronis et al. | 530/314 |

FOREIGN PATENT DOCUMENTS 8939431  5/1990  Australia.

OTHER PUBLICATIONS

Wilhelm, *Annual Review of Medicine*, vol. 22, 1971, pp. 63–84.
Polosa, *Allergy*, 1993, 48, pp. 217–225.
Hargreaves, et al, *Clin Pharmacol Ther*, Dec. 1988, pp. 613–621.
J. M. Stewart, et al., "Peptides 1992", *ESCOM*, C.H. Schneider and A.N. Eberle, eds., Leiden, 691–692, (1993).
Vavrek, et al., *Peptides*, 6, 161–164, (1985).
Zeitlin, et al., *Gut*, 14, 133, (1973).

*Primary Examiner*—Cecilia J. Tsang
*Assistant Examiner*—S. G. Marshall
*Attorney, Agent, or Firm*—Cushman Darby & Cushman IP Group of Pillsbury Madison & Sutro LLP

[57] ABSTRACT

The present invention pertains to modified bradykinin antagonist peptides of the formula $X\text{-}A^0\text{-}B^1\text{-}C^2\text{-}D^3\text{-}E^4\text{-}F^5\text{-}G^6\text{-}H^7\text{-}J^8\text{-}K^9$, where at least one of $F^5$, $H^7$ and $J^8$ is an indane substituted amino acids.

10 Claims, No Drawings

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Xaa  Arg  Pro  Xaa  Gly  Xaa  Ser  Xaa  Xaa  Arg
 1                   5                        1 0
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Xaa  Arg  Pro  Xaa  Gly  Xaa  Ser  Xaa  Xaa  Arg
 1                   5                        1 0
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Arg  Pro  Pro  Gly  Phe  Ser  Pro  Phe  Arg
 1                   5
```

( 2 ) INFORMATION FOR SEQ ID NO:4:

( i ) SEQUENCE CHARACTERISTICS:

(A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Arg Pro Xaa Gly Xaa Ser Xaa Xaa Arg
    1               5

(2) INFORMATION FOR SEQ ID NO:5:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

Xaa Xaa Arg Pro Xaa Gly Xaa Ser Xaa Xaa Arg
    1               5                   1 0

(2) INFORMATION FOR SEQ ID NO:6:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Xaa Xaa Arg Pro Xaa Gly Phe Ser Xaa Xaa Arg
    1               5                   1 0

(2) INFORMATION FOR SEQ ID NO:7:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Xaa Arg Pro Xaa Gly Xaa Lys Xaa Xaa Arg
    1               5                   1 0

(2) INFORMATION FOR SEQ ID NO:8:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Xaa Arg Pro Xaa Gly Xaa Ser Xaa Tyr Arg
    1               5                   1 0

(2) INFORMATION FOR SEQ ID NO:9:

(i) SEQUENCE CHARACTERISTICS:

(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

Xaa Arg Pro Xaa Gly His Ser Xaa Xaa Arg
1               5                   10

(2) INFORMATION FOR SEQ ID NO:10:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

Arg Arg Pro Xaa Gly Xaa Ser Xaa Xaa Arg
1               5                   10

(2) INFORMATION FOR SEQ ID NO:11:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

Xaa Xaa Arg Pro Xaa Gly Xaa Lys Xaa Xaa Arg
1               5                   10

(2) INFORMATION FOR SEQ ID NO:12:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

Xaa Xaa Arg Pro Xaa Gly Xaa Thr Xaa Xaa Arg
1               5                   10

(2) INFORMATION FOR SEQ ID NO:13:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:13:

Xaa Xaa Arg Pro Xaa Gly Xaa Glu Xaa Xaa Arg
1               5                   10

(2) INFORMATION FOR SEQ ID NO:14:

(i) SEQUENCE CHARACTERISTICS:

( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

```
Xaa  Xaa  Arg  Pro  Xaa  Gly  His  Ser  Xaa  Xaa  Arg
 1                  5                        10
```

( 2 ) INFORMATION FOR SEQ ID NO:15:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

```
Xaa  Arg  Arg  Pro  Xaa  Gly  Xaa  Ser  Xaa  Xaa  Arg
 1                  5                        10
```

( 2 ) INFORMATION FOR SEQ ID NO:16:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:16:

```
Xaa  Xaa  Arg  Pro  Xaa  Gly  Xaa  Ser  Xaa  Trp  Arg
 1                  5                        10
```

( 2 ) INFORMATION FOR SEQ ID NO:17:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:17:

```
Xaa  Xaa  Arg  Pro  Xaa  Gly  Xaa  Lys  Xaa  Xaa  Arg
 1                  5                        10
```

( 2 ) INFORMATION FOR SEQ ID NO:18:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:18:

```
Xaa  Arg  Arg  Pro  Xaa  Gly  Xaa  Ser  Xaa  Xaa  Arg
 1                  5                        10
```

( 2 ) INFORMATION FOR SEQ ID NO:19:

( i ) SEQUENCE CHARACTERISTICS:

(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:19:

```
Xaa Xaa Arg Pro Xaa Gly Xaa Ser Xaa Tyr Arg
 1           5               10
```

BRADYKININ ANTAGONIST PEPTIDES CONTAINING INDANE-SUBSTITUTED AMINO ACIDS

The U.S. Government has a paid-up license in this invention and the right in limited circumstances to require the patent owner to license others on reasonable terms as provided for by the terms of Grant No. HL-26284 awarded by the Department of Health, Education and Welfare.

BACKGROUND OF THE INVENTION

The invention relates to novel biologically active peptides which act as antagonists of the biological activities of bradykinin and its homologs and congeners, the pharmaceutically acceptable salts of these antagonists, and their application as therapeutic agents.

Bradykinin (BK), a nonapeptide (SEQ ID:3) ($Arg^1$-$Pro^2$-$Pro^3$-$Gly^4$-$Phe^5$-$Ser^6$-$Pro^7$-$Phe^8$-$Arg^9$) and its physiologically important related peptides, kallidin (Lys-bradykinin) and Met-Lys-bradykinin, exhibit physiological actions which qualify them as mediators of inflammatory reactions, hypotensive states, and pain. Bradykinin is overproduced in pathological conditions such as septic (Robinson et al., *Am. J. Med.* 59: 61 (1975)) and hemorrhagic (Hirsch et al., *J. Surg. Res.* 17: 147 (1974)) shock, anaphylaxis (Collier and James, *J. Physiol.* 160: 15P (1966)), arthritis (Jasani et al., *Ann. Rheum. Dis.* 28: 497 (1969); Hamberg et al., *Agents Actions* 8: 50( 1978); Sharma et al., *Arch. Int. Pharmacodyn.* 262: 279 (1983)), rhinitis (Proud et al., *J. Clin. Invest.* 72: 1678 (1983); Naclerio et al., *Clin. Res.* 33: 613A (1985)), asthma (Christiansen et al., *J. Clin. Invest.* 79: 188 (1987)), inflammatory bowel disease (Zeitlin and Smith, *Gut* 14: 133 (1973)), and certain other conditions including acute pancreatitis, post-gastrectomy dumping syndrome, carcinoid syndrome, migraine, and hereditary angioedema (Leme, Handb. Exp. Pharmacol. 50/I: 464 (1978)). The production of bradykinin results in pain at the site of the pathological condition, and the overproduction intensifies the pain directly or via stimulation by bradykinin of the activation of the arachidonic acid pathway which produces prostaglandins and leukotrienes, more distal mediators of inflammation (Handbook of Experimental Pharmacology, Vol. 25, Springer-Verlag (1969), and Vol. 25 Supplement (1979); Stewart, in "Mediators of the Inflammatory Process," Henson and Murphy, eds., Elsevier, (1989)).

Bradykinin has been found to be produced in inflammatory reactions in the intestine, provoking contraction of smooth muscle and secretion of fluid and ions. The existence of specific bradykinin receptors in the mucosal lining of the intestine and in intestinal smooth muscle is demonstrated by Manning et al. (*Nature* 229: 256 (1982)), showing the influence of bradykinin in very low concentrations upon fluid and ion secretion.

The production of bradykinin and associated pain in angina has been studied and reported (Kimura et al., *Amer. Heart J.* 85: 635 (1973); Staszewska-Barczak et al., *Cardiovasc. Res.* 10: 314 (1976)). The reported action of bradykinin and prostaglandins acting in concert are the natural stimulus for excitation of the sensory receptors signalling the pain of myocardial ischemia.

Bradykinin and bradykinin-related kinins are not only produced endogenously, but may also be injected into an animal via stings or bites. It is known that insects such as hornets and wasps inject bradykinin related peptides that cause pain, swelling and inflammation.

Bradykinin and related peptides exert their actions on biological systems by combining with specific receptors on cell membranes in the affected tissues. These receptors are of two classes, designated B1 and B2. The B2 receptors require the entire bradykinin sequence for effective receptor combination and production of the biological effects, whereas the B1 receptors do not respond to intact bradykinin, but respond selectively to bradykinin lacking the carboxy-terminal arginine residue; this peptide is designated [des-$Arg^9$]-bradykinin. [des-$Arg^9$]-Bradykinin is produced in the body by one of the enzymes that normally destroys bradykinin, the plasma enzyme carboxypeptidase N, that removes the carboxy-terminal arginine residue. Essentially all normal physiological responses and many pathophysiological responses to bradykinin are mediated by B2 receptors, whereas in certain damaged tissues and in certain kinds of chronic inflammation, B1 receptors are induced. The currently accepted wisdom is that bradykinin antagonist drugs for treatment of chronic inflammation must have antagonist action at both B1 and B2 receptors.

The search for understanding of the mechanisms of action of bradykinin, which is essential for the development of useful tools for diagnostic use, and for the development of therapeutic agents aimed at alleviating the intense pain and other symptoms caused by the overproduction of bradykinin, was severely hindered by the lack of specific sequence-related competitive antagonists of bradykinin until the discovery of the first effective bradykinin antagonists by Vavrek and Stewart in 1985 (Vavrek et al., *Peptides* 6:161–164 (1985); U.S. Pat. No. 4,693,993). In these early antagonists, the proline residue at position 7 of bradykinin was replaced by a D-aromatic amino acid residue, usually D-phenylalanine or D-thienylalanine. Subsequently, many modifications of the original bradykinin antagonists have been described (reviewed by J. M. Stewart and R. J. Vavrek in R. M. Burch, ed., "Bradykinin Antagonists," Pergamon, 1990), but most effective antagonists have had an aromatic amino acid residue at positions 5 and 8 and a D-aromatic residue at position 7. In certain antagonists, positions 5, 7, and 8 are occupied by aliphatic amino acid residues (J. M. Stewart, et al. in "Peptides 1992," C. H. Schneider and A. N. Eberle, eds., ESCOM, Leiden, 1993, pp 691–692).

Antagonists for bradykinin B1 receptors are obtained by replacing the phenylalanine residue at position 8 of [des-$Arg^9$]-bradykinin by an aliphatic amino acid, such as leucine. Thus, [$Leu^8$, des-$Arg^9$]-bradykinin and Lys-[$Leu^8$, des-$Arg^9$]-bradykinin are effective B1 receptor antagonists. All of the bradykinin antagonists of the type described by Stewart and Vavrek, containing a D-amino acid residue at position 7, act only upon B2 receptors. In certain in vivo assays, some of these early antagonists were shown to act upon both B2 and B1 receptors, but it was demonstrated that those antagonists were substrates for carboxypeptidase N, and that the antagonist action on B1 receptors occurred only after cleavage of the antagonist to the [des-$Arg^9$]analog. Newer, more potent, types of bradykinin antagonists contain residues at position 8 (such as Cpg, Oic) that block the degradative action of carboxypeptidase N; these antagonists have no action at B1 receptors. The present art of bradykinin antagonist peptides has not described any B1 antagonists that possess a carboxy-terminal arginine residue. Certain of the bradykinin antagonists described in this application that do contain the carboxy-terminal arginine residue have been found to possess high antagonist activity at both B1 and B2 receptors. This discovery runs counter to all principles generally accepted in the state of the art of bradykinin antagonists. Notwithstanding prior efforts, there remains a considerable need to provide improved B1 and B2 receptor antagonists. A main object of the present invention is to provide such receptor antagonists which include indaneglycine substituted bradykinin antagonists demonstrating B1 receptor and B2 receptor antagonist activity with high potency and broad specificity of antagonism.

SUMMARY OF THE INVENTION

The invention provides novel bradykinin antagonist peptides whereby, in the conventional bradykinin nomenclature, the amino acid residues at at least one of positions 5, 7, and 8, individually, pairwise or collectively, are replaced with indane-substituted glycine residues:

$$X-A^0-B^1-C^2-D^3-E^4-F^5-G^6-H^7-J^8-K^9-Z$$

Wherein

X is optionally absent but, if present, is an aromatic, aliphatic, aromatic-aliphatic, alicyclic, heterocyclic or urethane-type acylating group, a guanidyl group, or at least one amino acid;

$A^0$, $B^1$, $C^2$, $D^3$, $E^4$, $G^6$ and $K^9$ are aromatic, aliphatic, heterocyclic, or alicyclic amino acids;

Z is optionally absent but, if present, is at least one amino acid; and at least one of $F^5$, $H^7$ or $J^8$ is replaced with an indane-substituted glycine residue.

DETAILED DESCRIPTION OF THE INVENTION

The present invention provides modified bradykinin antagonist peptides that contain amino acids substituted on the α-carbon or on the α-nitrogen by 1-indanyl or 2-indanyl groups. In a preferred embodiment, the bradykinin antagonist peptides of the present invention contain indane-substituted amino acid residues at positions five, seven and eight of the bradykinin native sequence. Certain of these novel bradykinin analog peptides have been discovered to exhibit unanticipated high potency and broad specificity of antagonism against bradykinin action, both in vitro and in vivo.

The bradykinin antagonist peptides of the present invention are characterized as follows:

$$X-A^0-B^1-C^2-D^3-E^4-F^5-G^6-H^7-J^8-K^9-Z$$

Wherein

X is the amino-terminal amino group or an aromatic, aliphatic, aromatic-aliphatic, alicyclic, heterocyclic or urethane-type acylating group, a guanidyl group, a single amino acid of the D- or L- configuration, or a di- or poly-peptide containing amino acids of the D- or L-configuration, or a combination of these, $A^0$ is D-Arg or another basic or neutral aromatic, aliphatic, heterocyclic or alicyclic amino acid of the D- or L-configuration, B is Arg or another basic or neutral aromatic, aliphatic, heterocyclic or alicyclic amino acid of the D- or L-configuration, C is Pro, Hyp, or another basic or neutral aromatic, aliphatic, heterocyclic, or alicyclic amino acid of the D- or L- configuration, D is Pro, Hyp, or another basic or neutral aromatic, aliphatic, heterocyclic, or alicyclic amino acid of the D- or L- configuration, E is Gly, Niga, Nigb or another basic or neutral aromatic, aliphatic, heterocyclic, or alicyclic amino acid of the D- or L- configuration, F is Igla, Iglb, Niga, Nigb, Phe, Thi, Cpg, Chg, or another aliphatic, aliphatic heterocyclic, or alicyclic amino acid of the D- or L- configuration, G is Ser, Ser(SO), HBQ or another aromatic, aliphatic, heterocyclic, or alicyclic amino acid of the D- or L-configuration, H is D-Igla, D-Iglb, Niga, Nigb, D-Tic, D-Cpg, D-Chg, or another aliphatic, aliphatic heterocyclic, or alicyclic amino acid of the D-configuration, J is Igla, Iglb, Niga, Nigb, Tic, Nbn, Oic, Cpg, Chg, or another aromatic, aliphatic, aliphatic heterocyclic, or alicyclic amino acid of the D- or L- configuration, K is Arg or another basic or neutral aromatic, aliphatic, heterocyclic or alicyclic amino acid of the D- or L- configuration, and Z is the carboxy-terminal carboxyl group or a carboxy-terminal extension composed of an amino acid of the D- or L-configuration or a peptide composed of amino acids of the D- or L-configuration.

According to the above formula, X and Z may be alternatively described as being optionally absent in which case they may represent the terminal amino and carboxy groups, respectively.

The bradykinin antagonist peptides of the present invention may be illustrated by the following (alignment of the residues in a particular row does not imply nor limit to a given peptide sequence):

| X-- | A--0 | B--1 | C--2 | D--3 | E--4 | F--5 | G--6 | H--7 | J--8 | K--9 | Z |
|---|---|---|---|---|---|---|---|---|---|---|---|
| Aaa | DArg | Arg | Pro | Hyp | Gly | Igla | Ser | DIgla | Igla | Arg | |
| Aca | DLys | Lys | DMF | Pop | Iglb | Ser(SO) | DIglb | Iglb | Lys | DArg | |
| Acetyl | Arg | DArg | NMF | Niga | Nigb | Niga | HBQ | Niga | Niga | | |
| Dhq | Lys | DLys | MPIV | MPIV | Ala | Nigb | Cys | Nigb | Nigb | | |
| Nba | | | Hyp | Pro | Gly | Leu | Gly | DLeu | Leu | | |
| Tba | | | Azt | Azt | | Chg | DIglb | DChg | Chg | | |
| Cha | | | Dhp | Dhp | | Ile | | DIle | Ile | | |
| Cpa | | | Inip | Inip | | Val | | DVal | Val | | |
| Gun | | | Thz | Thz | | Alg | | DCpg | Cpg | | |
| | | | Pop | | | Oic | | DOic | Oic | | |
| | | Lys-Lys | | | | Pop | | DPop | Pop | | |
| | | | | | | Nle | | DNle | Nle | | |
| | | | | | | DMF | | DDMF | | | |
| | | | | | | | | Iglb | | | |

Wherein

In a preferred embodiment, the bradykinin antagonist peptides of the present invention are represented as follows:

X-Basic$^0$-Basic$^1$-Pro$^2$-Pro$^3$-Gly$^4$-Indanyl$^5$-Ser$^6$-DIndanyl$^7$-Indanyl$^8$-Basic$^9$ where "Indanyl" is a glycine residue substituted on either the α-carbon or the α-nitrogen by a 1-indanyl or a 2-indanyl moiety, and "Basic" indicates a basic amino acid residue, such as, for example, arginine or lysine.

A more preferred embodiment may be represented as follows (SEQ ID No:1):

H-DArg$^0$-Arg$^1$-Pro$^2$-Hyp$^3$-Gly$^4$-Iglb$^5$-Ser$^6$-DIglb$^7$-Iglb$^8$-Arg$^9$.

Salts of the described bradykinin antagonist peptides include salts with HCl, TFA, HOAc, as well as other pharmaceutically acceptable salts.

According to this invention, the indane substituent can be on either the α-carbon (residues abbreviated Igl) or the nitrogen (residues abbreviated Nig) of the glycine residue, and the indane residue can be attached to the glycine moiety at either position 1 (Igla or Niga) or position 2 (Iglb or Nigb) of the indane group.

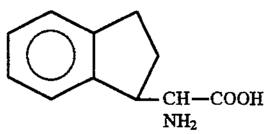

Igla

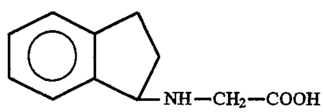

Niga

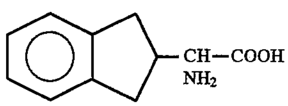

Iglb

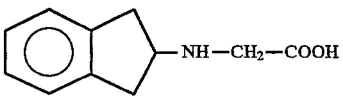

Nigb

These indaneglycine substitutions in bradykinin antagonist peptides were made in addition to and in combination with other substitutions in bradykinin antagonist peptides known to those skilled in the art to yield effective antagonists of the biological actions of bradykinin. Several of the new bradykinin analogs containing indaneglycine were found to possess unexpectedly high potency in biological test systems. Also without precedent was the finding that certain of these novel bradykinin analogs were highly effective antagonists of bradykinin at both B1 and B2 receptors.

Often both B2 and B1 receptors are present on the same cells and when activated by either bradykinin or [des-Arg$^9$]-bradykinin, the response produced is similar, e.g. vasodilatation or pain. B1 in addition to B2 receptors have been shown to mediate hypotension in animal models of sepsis and endotoxin shock (Regoli et al., *Eur. J. Pharmacol.,* 71: 105 (1981); Marceau et al., *Pharmacology,* 29:70 (1983); Nwator & Whalley, *Eur. J. Pharmacol.,* 160:125 (1989)); Siebeck et al., *Adv. Expy. Med. Biol.,* 247:389 (1989)); prostacyclin and nitric oxide release from endothelial cells (D'Orlean Juste et al., *Br. J. Pharmacol.,* 96:920 (1989); Wiemer & Wirth, *J. Pharm. Exp. Therap.,* 262:729 (1992)); edema (Neppl et al., *Acta Physiol. Scand.,* 142:141 (1991)); Manitone & Rodrigues, *Bt. J. Pharmacol.,* 99:516 (1990)); bone resorption (Ljunggren & Lerner, *Br. J. Pharmacol.,* 101:382 (1990)); stimulation of human gingival fibroblasts (Lerner & Moderer, *Inflammation,* 15:427 (1991)); release of inflammatory cytokines from macrophages (Burch et al., *Agents & Actions.,* 27:258 (1989)); hyperalgesia in acute and chronic inflammation (Dray & Perkins, *Trends Neurosci.,* 16:99 (1993)); Correa & Calixto, *Br. J. Pharmacol.,* 110:193 (1993), Cruwys et al., *Br. J. Pharmacol.,* 113:940 (1994); upregulation in antigen arthritis (Farmer et al., *Agents & Actions,* 34:191 (1991)); airways hyperreactivity and inflammatory cell influx into the lung (Farmer et al., *Br. J. Pharmacol.,* 107:653 1992)); contraction of the human colon, and non-pregnant and pregnant uterus (Couture et al., *Can, J. Physiol. Pharmacol.,* 59:957 (1981)); Abbas et al., *Brit J. Pharmacol.,* 112:433P (1993)); contraction of myofibroblasts (Appleton et al., Proc. of the Second International Symposium on cGRP-Peptides and Their Antagonists in Tissue Injury (Montreal, Aug.1994)); contraction of cerebral blood vessels (Whalley et al., *Naunyn-Schmiedebergs Arch. Pharmacol.,* 324:296 (1983)). (See also Hall *Pharmac. Ther.* 56:131–190 (1992).

This invention also provides methods of treating and/or preventing disease conditions where the B1 and/or B2 receptor is implemented. Compounds with antagonist activity against both B2 and B1 receptors would be preferable than single receptor antagonist compounds in certain chronic diseases states. Based on the above description of B1 and B2 receptor involvement in disease, the compounds of the present invention are expected to be effective in treating SIRS (Systemic Inflammatory Response Syndromes)/sepsis, polytrauma, inflammatory bowel disease, acute and chronic pain, bone destruction in rheumatoid and osteo arthritis and periodontal disease, dysmenorrhea, premature labor, brain edema following focal injury, diffuse axonal injury, stroke, reperfusion injury and cerebral vasospasm after subarachnoid hemorrhage, allergic disorders including asthma, adult respiratory distress syndrome, wound healing and scar formation.

As used herein, abbreviations of the natural amino acids are those accepted in the art (*Biochem. J.* 126:773 (1972)), and unless prefixed with D are all of the L-configuration (except glycine and MPIV, which are not optically active).

Abbreviations used for unnatural amino acids in Bradykinin analogs are indicated below:

| | |
|---|---|
| AC6 | 1-Aminocyclohexane-1-carboxylic acid |
| Aoc | 2-Azabicylo (3.3.0) octane-3-carboxylic acid |
| Alg | Allylglycine |
| Azt | Azetine-2-carboxylic acid (norproline) |
| cAcp | 2-Aminocyclopentane-1-carboxylic acid |
| CDF | p-Chloro-D-Phe |
| Chg | CyclohexylGly (α-Aminocyclohexaneacetic acid) |
| cLeu | 1-Aminocyclopentane-1-carboxylic acid (cycloleucine) |
| Cpg | CyclopentylGly (α-Aminocyclopentaneacetic acid) |
| Dhp | 3,4-Dehydro-Pro |
| DMF | 2,4-Dimethylphenylalanine |
| DMTP | 5,5-Dimethyl-4-thiaproline |
| Eac | 6-Aminohexanoic acid (ε-aminocaproic acid) |
| FDF | p-Fluoro-DPhe |
| HBQ | N5-(4-hydroxybutyl)-glutamine |
| Hig | Hexahydroindanylglycine |
| Hyp | trans-4-Hydroxy-Pro |
| Ica | Indole 2-carboxylic acid |
| Igla | α-(1-indanyl)glycine |
| Iglb | α-(2-indanyl)glycine |
| Inip | Isonipecotic acid (piperidine-4-carboxylic acid) |
| Mag | α-Methallylglycine |
| MDY | O-Methyl-DTyr |
| MEF | 2,3-Methano-E-phenylalanine |
| MPIV | 2,4-Methanoproline (2-Azabicyclo-(2,1,1)-hexane-1-carboxylic acid) |
| Nal | β-2-Napthyl-Ala |
| Nia | N-(2-indanyl)-alanine |
| Niga | N-(1-indanyl)glycine |
| Nigb | N-(2-indanyl)glycine |
| Nle | Norleucine |
| NMF | N-Methylphenylalanine |
| Oic | Octahydroindole-2-carboxylic acid |
| OMT | O-Methyl-Tyr |
| Pal | β-3-Pyridyl-Ala |
| PCF | p-Chloro-Phe |

| | |
|---|---|
| Pip | Pipecolic acid ("homo-Pro") |
| Pop | trans-4-PropoxyPro |
| Ser(SO) | Serine-O-sulfate |
| Suc | Succinyl |
| Thi | β-2-Thienyl-Ala |
| Thz | Thiazolidine-4-carboxylic acid |
| Tic | 1,2,3,4-Tetrahydroisoquinoline-3-carboxylic acid |
| TMF | 2,4,6-Trimethylphenylalanine |

Abbreviations used for derivatizing groups (as used for "X") are as follows:

| | |
|---|---|
| Aaa- | 1-Adamantaneacetyl- |
| Ac- | Acetyl- |
| Aca- | i-Adamantanecarboxyl- |
| Bpg- | N,N'-bis-Pentamethyleneguanidyl- |
| Bz- | Benzoyl- |
| Cha | Cyclohexaneacetyl- |
| Cpa- | Cyclopentaneacetyl- |
| Dca- | 2,2-Dicyclohexylacetyl- |
| Dcg- | N,N'-Dicyclohexylguanidyl- |
| Dhq- | 2,3-Dehydroquinuclidine-3-carboxyl- |
| Dpa | 2,2-Diphenylacetyl |
| Dpp- | 3,3-Diphenylpropionyl- |
| Gun- | Guanidyl |
| Nba- | Norbornane-2-acetyl- |
| Nbc- | 2-(cis-5-norbornene-endo-3-carboxyl)- |
| Nbi- | cis-5-norbornene-endo-2,3-dicarboximidyl- |
| Paa- | Phenylacetyl- |
| Pba- | 4-Phenylbutyryl- |
| Ppa- | 3-Phenylpropionyl- |
| Sin- | Sinapinyl-(3,5-dimethoxy-4-hydroxycinnamyl-) |

The description of peptide synthesis methods uses several abbreviations for standard solvents, reagents and procedures, defined as follows:

| | |
|---|---|
| BOP | Benzotriazolyloxy-tris-(dimethylamino)phosphonium hexafluorophosphate |
| BuOH | n-Butanol |
| DCC | Dicyclohexylcarbodiimide |
| DCM | Dichloromethane |
| DIC | Diisopropylcarbodiimide |
| DIEA | Diisopropylethyl amine |
| DMF | Dimethylformamide |
| HATU | O-(7-azabenzotriazol-1-yl)-1,1,3,3-tetramethyluronium hexafluorophosphate |
| HOAc | Acetic acid |
| MeOH | Methanol |
| OHMR | Hydroxymethylpolystyrene resin for peptide synthesis, 1% crosslinked. |
| TBTU | O-(benzotriazol-1-yl)-1,1,3,3-tetramethyluronium tetrafluoroborate |
| TEA | Triethyl amine |
| TFA | Trifluoroacetic acid |

The following abbreviations for blocking groups used in synthesis are:

| | |
|---|---|
| Boc | t-Butyloxycarbonyl |
| Tos | p-Toluenesulfonyl |
| Bzl | Benzyl ether |

The following abbreviations for standard techniques used are:

| | |
|---|---|
| AAA | Amino acid analysis (Stewart & Young p. 108) |
| CCD | Countercurrent distribution (Stewart & Young p. 96) |
| ELEC | Paper electrophoresis (Stewart & Young p. 117) |
| HPLC | High performance liquid chromatography (Stewart & Young, p. 100) |
| Kaiser test | Ninhydrin test for completeness of coupling reactions (Stewart & Young, p. 105) |
| SPPS | Solid phase peptide synthesis |
| TLC | Thin-layer chromatography (Stewart & Young, p. 103) |

The synthesis of peptides described herein, including preparation of appropriate amino acid derivatives, their activation and coupling to form peptides and methods for purification of peptides and determination of their purity are included in the general body of knowledge of peptide chemistry, as generally described in Houben-Weyl "Methoden der Organischen Chemie" Vol. 16, parts I & II, (1974) for solution-phase synthesis, and in "Solid Phase Peptide Synthesis" by Stewart and Young (1984) for synthesis by the solid phase method. A chemist skilled in the art of peptide synthesis would be able to synthesize the described peptides by standard solution methods or by manual or automatic solid phase methods. The invention is described further by the following examples which are intended to be illustrative and instructive and in no way intended to be limiting.

EXAMPLES

Example I

Peptide Synthesis - General Methods

Synthesis of the bradykinin antagonist peptides of the present invention by solid phase peptide synthesis (SPPS) may be carried out manually (see Stewart & Young) or by use of the Beckman Model 990, Biosearch Model 9500 or other automatic peptide synthesizers. SPPS involves use of certain standard procedures, defined as follows:

Procedure A: DCC coupling reaction: (Described in Stewart & Young, p 76 ff). A 2.5-fold excess of Boc-amino acids over peptide-resin is used in the Model 990 synthesizer. Boc-amino acids are activated for coupling with an equimolar amount of DCC. The solvent may be DCM or mixtures of DCM and DMF. Completeness of coupling may be determined by use of the Kaiser reagent.

Procedure B: DIC coupling: In the Model 9500 synthesizer a 6-fold excess of Boc-amino acids over peptide-resin is used with an equimolar amount of DIC. The solvent is DCM:DMF (1:1). The resin is washed with the same solvent before and after coupling. Completeness of coupling is determined with the Kaiser reagent.

Procedure C: BOP, TBTU or HATU coupling reaction for hindered amino acids: A 3-fold excess of Boc-amino acid over peptide-resin is mixed with an equimolar amount of BOP, TBTU or HATU and 2 equivalents of DIEA in DMF. The peptide-resin is washed with DMF before and after the coupling reaction, and after coupling is then washed 2 times with methanol before continuing standard DCM washes. Completeness of coupling is checked by the Kaiser test. BOP, TBTU and HATU, in this order, show increasing ability to cause successful coupling of sterically hindered amino acids.

Procedure D: TFA deprotection and neutralization: (Stewart & Young p. 76). The deprotection reagent is TFA:DCM (1:3), containing 1 mg/ml indole. It is used for 30 minutes, following a prewash. The neutralization reagent is 10% TEA in DCM, prepared fresh and used twice for one minute.

Procedure E: Terminal deprotection: (Described by Stewart & Young, p. 79). Deprotection with TFA:DCM is carried out as described in Procedure D. The peptide-resin is then washed three times with DCM and three times with MeOH and dried.

Procedure F: HF cleavage and deblocking: (Stewart & Young p. 85). A batch of 500 mg (0.2 mmole) of peptide-resin is mixed with 1.0 ml anisole and chilled in the reaction vessel to −78C. and 10 ml of anhydrous HF is distilled into the vessel under vacuum. The mixture is stirred at 0 C. for 45 min, and the HF is evaporated under vacuum. The peptide and resin mixture is washed three times with dry ether, and the peptide is extracted into glacial HOAc. The peptide solution is lyophilized.

Procedure G: PURIFICATION OF PEPTIDES: (Stewart & Young p. 96). The peptides may be purified by CCD for 100 transfers in the appropriate system, as determined by preliminary k estimation. Examples of CCD systems are:

A: n-BuOH:1% TFA for average antagonist peptides

B: n-BuOH:ethyl acetate:1% TFA (1:1:2) for more hydrophobic antagonist peptides.

Procedure H: TLC: TLC may be carried out on silica gel plates with systems F (n-BuOH:HOAc:$H_2O$: pyridine= 15:3:8:10) and I (n-BuOH:HOAc:$H_2O$=4:1:1). Chlorine-tolidine and Sakaguchi spray reagents may be used. (Stewart & Young, p. 120).

Procedure J: Paper electrophoresis (ELEC): ELEC may be done in buffers of Ph 2.8 and 5.0 as described in Stewart & Young. Chlorine-tolidine and Sakaguchi spray reagents may be used.

Procedure K: HPLC: Preparative HPLC may be carried out on large-pore reversed phase C4 or C8 silica columns in a gradient of 0.1% TFA in $H_2O$ to 0.08% TFA in acetonitrile. Detection may be by UV at 214 or 235 nm. Analytical HPLC may be carried out in the same system and in a gradient of acetonitrile in 0.25M triethylammonium phosphate, pH 6.5.

Procedure L: MASS spectroscopy: Peptides may be checked for the correct molecular mass by fast atom bombardment (FAB) or laser desorption (MALDI) mass spectroscopy.

Procedure M: Amino acid analysis (AAA): Peptides may be hydrolyzed in 6N HCl and analyzed as described in Stewart & Young, pp 109–112, using a Beckman Model 6300 amino acid analyzer.

Example II

Synthesis of α-(2-indane)-glycine (Iglb)

2-Bromoindane: To 2-indanol (Aldrich) (105 g, 0.78 mol) in pyridine (16 mL, 0.2 mol) and 340 mL of chloroform at −15 C. was added $PBr_3$ (84 mL, 0.89 mol) over 45 min. The reaction mixture was stirred overnight at room temperature and extracted by addition of 450 mL of chloroform and 500 g of ice. The organic layer was washed twice with water, and dried over $Na_2SO_4$. The solvent was evaporated in vacuo, leaving a brown semi-solid. The product was distilled rapidly in vacuo and then fractionated to give 69 g (45%) 2-bromoindane, bp 90–93 /3 mmHg; $n_d^{23}$=1.5837.

Ethyl α-acetamido-α-cyano-2-indaneacetate: To sodium ethoxide (20.4 g, 0.3 mol), suspended in dry DMSO (250 mL) was added a solution of ethyl acetamidocyanoacetate (50 g, 0.294 mol) in 250 mL dry DMSO, with vigorous stirring. Then 2-bromoindane (65.0 g, 0.33 mol) was added dropwise during 40 min, with vigorous stirring. The brown solution was stirred overnight at room temperature and 4 h at 50 C. The mixture was evaporated in vacuo and the residue was treated with 300 mL cold water and extracted twice with 250 mL of EtOAc. The combined extracts were dried ($MgSO_4$) and evaporated to give the crude product, 70.7 g brown solid. The first recrystallization from EtOH/$H_2O$ gave 58.6 g yellowish solid, mp 153–157. The second recrystallization from toluene gave 54.6 g (64.9%) white flakes, mp 159–161 C.

D,L-2-indaneglycine: A solution of 54.6 g (0.19 mol) ethyl α-acetamido-α-cyano-2-indaneacetate in 820 mL of 10% NaOH was refluxed for 20 h. The solution was cooled, decolorized with carbon, and the filtrate, in an ice bath, was adjusted to pH 6.5 with conc. HCl (about 150 mL), using a pH meter, and further chilled to complete precipitation of the product, which was filtered and washed with cold water, methanol and ether; 36.4 g. The solid was refluxed in 1200 mL 6N HCl for 10 h; the solution was decolorized with carbon and chilled to give a precipitate, which was collected and recrystallized from $H_2O$ to give 22.6 g product. Additional product was obtained from the mother liquor to give 31.7 g (86.9%) of D,L-2-indaneglycine.

N-acetyl-D,L-2-indaneglycine: To a mixture of 6.83 g (0.03 mol) of D,L-2-indaneglycine and 54 mL $H_2O$ was added 30 mL (0.06 mol) 2N NaOH. The solution was chilled and stirred while 1.4 mL (0.015 mol) acetic anhydride was added. Seven successive additions of 2N NaOH (14 mL) and 1.4 mL of acetic anhydride were done over 30 min, and the solution was allowed to warm to room temperature, with continued stirring. Stirring was continued overnight. The solution was chilled and acidified to pH 3 with 6N $H_2SO_4$ (40 mL). After standing in the cold, the precipitate was collected and washed with a small amount of cold $H_2O$; 7.95 g, mp 199–202. The product was recrystallized from acetone/petroleum ether (30–60) to give 7.8 g acetyl D,L-2-indaneglycine, mp 201–203.

Resolution of D,L-2-indaneglycine: N-acetyl-D,L-2-indaneglycine (7.0 g, 0.03 mol) was suspended in 300 mL $H_2O$, and the pH was adjusted to 7.6 with 4N LiOH (9 mL). Water was added to a volume of 350 mL, the solution was thermostatted at 37 C., with stirring, and hog kidney acylase I (Sigma A-3010, 50 mg) was added. The pH was maintained at 7.6 by addition of LiOH; after precipitation of L-indaneglycine began, the pH rose and was brought back with 0.1 N HOAc. After 5 h an additional 30 mg acylase I was added, and after 24 h an additional 20 mg acylase was added, with continued pH control. Incubation, with stirring was for a total of 36 h. The solution was cooled to room temperature, and 250 mL cold water and 500 mL EtOAc were added. The mixture was carefully acidified to pH 0.75 with 6 N HCl (about 25 mL). The two layers were wet filtered through Celite and separated. The water phase was extracted twice with EtOAc (250 mL).

The aqueous solution was decolorized with carbon at 50 and evaporated under reduced pressure. The crystals were dissolved in 25 mL $H_2O$ and 25 mL 6 N HCl and the cold solution was brought to pH 5.5 with conc. $NH_4OH$. The product was collected, washed with cold water, and dried; 2.8 g (97.6%) L-2-indaneglycine; mp 302–305; $[\alpha]_d^{25}$=+35.4 (c 2, 2N HCl).

The ethyl acetate phase was washed with saturated NaCl solution, dried over $MgSO_4$ and evaporated in vacuo. The solid residue was recrystallized from EtOH/petroleum ether to give 3.1 g (88.6%) acetyl-D-2-indaneglycine, mp 210–212; $[\alpha]_d^{25}$= −38.7 (c 2, EtOH).

Acetyl D-2-indaneglycine (2.92 g, 0.0125 mol) was refluxed in 125 mL of 6 N HCl for 8 H. The solution was evaporated under reduced pressure at 40, and the residue was dissolved in 40 mL 6 N HCl and 150 mL $H_2O$. The solution was neutralized to pH 5.5 with conc. NH₄OH, and the white solid was collected, washed with cold water and dried in vacuo to yield 2.17 g (90.8%) of D-2-indaneglycine; mp 302–305; $[\alpha]_d^{23}$=–34.6 (c 2, 2N HCl).

Both the D- and L-isomers were converted to the N-Boc derivative by the standard procedure described in Example III. The mp and rotation of the compound is: mp 86°–89° C. (dec); $[\alpha]_D^{22}$=+16.9 (c2, EtOH).

Example III

Synthesis of N-Boc-N-(2-indanyl) glycine (Boc-Nigb)

Synthesis of N-(2-indanyl)-glycine (Nigb): Glycine methyl ester (3.49 g, 0.025 mole) and 2-indanone (4.96 g, 0.0375 mole) were dissolved in EtOH and then NaCNBH₃ (4.71 g, 0.075 mole) was added portionwise during about 30 min. The mixture was stirred at room temperature for 24 h. The EtOH was removed under reduced pressure and the residue was treated with water. The product was extracted by several extractions with EtOAc. The organic phase was washed with saturated aqueous NaHCO₃, dried over Na₂SO₄ and evaporated. The product was purified by chromatography over silica gel (EtOAc and EtOAc/MeOH =9:1) to give the crude ester as a colorless oil (2.46 g). The ester (2.43 g in 30 mL MeOH) was saponified with 15 mL 1N NaOH at room temperature for 5 h. The solution was concentrated and the residue was taken up in dioxane-water.

Synthesis of the Boc-derivative: The solution was cooled to 0 and treated with Boc anhydride (3.27 g, 0.015 mole) portionwise. The ice bath was removed, and the mixture was stirred overnight at room temperature, with adjustment of pH to 9.0 with NaOH solution as needed. The solution was evaporated to dryness under reduced pressure, the residue was taken up in EtOAc/water (70/30 mL), and the solution was treated with saturated aqueous citric acid solution to pH 2.5. The phases were separated and the water was extracted twice with EtOAc. The organic phase was washed with water, saturated NaCl solution, dried over Na₂SO₄ and evaporated under reduced pressure. The crude product was recrystallized from EtOAc/hexanes; 1.85 g (25.4%), mp 130–131 C.

Example IV

Synthesis and Derivatization of α-(1-Indane)Glycine

The D- and L-isomers of α-(1-indane)glycine were synthesized as described by Josien et al., *J. Med. Chem.* 37: 1586–1601 (1994). The synthetic procedures gave the optically pure D- and L-amino acids.

The amino acids were converted to the N-Boc derivatives by the standard procedure described in Example III; m.p. 109–111.

Example V

Synthesis and Derivatization of N-(1-Indanyl) Glycine

The amino acid was synthesized as described by Miyake, et al., *Takeda Kenkyushoho* 44: 171–185 (1985). [*Chem. Abstr.* 106: 156830 (1987)]. N-(1-indanyl)-benzylamine was prepared by reductive amination of 1-indanone with benzylamine, and alkylation of the amine by ethyl bromoacetate. The benzyl group was cleaved by hydrogenolysis over palladium. Saponification of the ethyl ester gave the amino acid, which was converted to the Boc derivative by the standard procedure described in Example III.

Alternatively, 1-indanone was reductively aminated with glycine methyl ester, followed by saponification of the ester.

The following examples are illustrative of compounds of this invention and are not limitative. All percentages and ratios are by weight when solids are involved and by volume when only liquids are involved.

Example VI

Synthesis of Compound 1-DArg-Arg-Pro-Hyp-Gly-Iglb-Ser-DIglb-O ic-Arg (SEQ ID NO:2)

The Model 990 synthesizer vessel was loaded with 1.66 g of Boc-Arg(Tos)-OHMR (0.24 mmol/g substitution; 0.4 mmol total). After deprotection and neutralization by Procedure D, Boc-L-Oic was coupled by Procedure C, using BOP as coupling agent. Coupling was checked for completeness with the Kaiser test, and may be repeated if necessary. In the same manner, Boc-D-Iglb, Boc-Ser(Bzl), Boc-Iglb, Boc-Gly, Boc-Hyp, Boc-Pro, Boc-Arg(Tos) and Boc-D-Arg(Tos) were coupled, using procedure C with BOP reagent. After deprotection by Procedure E, the peptide-resin was divided into 4 parts. The peptide was cleaved from one part of the resin and deblocked by Procedure F. The peptide was purified by CCD using Procedure G and System A. The purified peptide was checked for purity by TLC (Procedure H), ELEC (Procedure J) and HPLC (Procedure K), and characterized by AAA (Procedure M) and MASS (Procedure L). The other parts of the peptide-resin were used for synthesis of the derivatives in which acyl groups were attached to the amino-terminus of the peptide on the resin.

Example VII

Synthesis of Compound 2-Aca-DArg-Arg-Pro-Hyp-Gly-Iglb-Ser-DIg lb-Oic-Arg

Acylation of the peptide while on the resin: Using one part of the peptide-resin prepared in Example VI, Adamantanecarboxylic acid was coupled to the peptide using Procedure C with TBTU reagent to activate the Aca. The acylated peptide was cleaved from the resin, purified and characterized by the same procedures described in Example VI.

Example VIII

Synthesis of Compound 3-Dhg-DArg-Arg-Pro-Hyp-Gly-Iglb-Ser-DIg lb-Oic-Arg

Acylation of the pure peptide in solution: A sample of 25 mg of the pure peptide of Example VI was dissolved in 0.5 ml DMF and two equivalents of DIEA were added. 2,3-Dehydroquinuclidine-3-carboxylic acid (1.5 equivalents) was dissolved in 0.5 ml DMF and activated by addition of BOP reagent (1.5 equivalents) and DIEA (3 equivalents). After activation for 15 min at room temperature, the twoacylating mixture was added to the peptide solution. The solution was stirred overnight, and then evaporated in high vacuum. The acylated peptide was purified by HPLC (Procedure K) and characterized using Procedures H, J, L and M.

Example IX

Solid phase synthesis of Compound 4-DArg-Arg-Pro-Hyp-Gly-Iglb-Ser-DIglb-M PIV-Arg Use of HATU reagent for coupling a sterically highly hindered Boc-amino acid to a peptide-resin: The synthesis of this peptide was carried out as described in Example VI, except that the Boc-MPIV failed to couple to the Arg-resin when activated by BOP. Therefore Boc-MPIV was activated with HATU, when coupling proceeded well. The remainder of the synthesis was carried out with BOP reagent for activation. Cleavage, purification, and characterization of this peptide was done as in Example VI.

Example X

Using the same general procedures, the following peptides were synthesized, purified and characterized:

5. (SEQ ID NO:4) Arg-Pro-Hyp-Gly-Thi-Ser-DIglb-Oic-Arg
6. DArg-Arg-Pro-Hyp-Gly-Thi-Ser-Iglb-Oic-Arg
7. DArg-Arg-Pro-Hyp-Gly-Thi-Ser-DIglb-Oic-Arg
8. DArg-Arg-Pro-Hyp-Gly-Thi-Ser-DCpg-Iglb-Arg
9. DArg-Arg-Pro-Hyp-Gly-Thi-Ser-DCpg-DIglb-Arg
10. DArg-Arg-Pro-Hyp-Gly-Cpg-Ser-DCpg-Iglb-Arg
11. DArg-Arg-Pro-Hyp-Gly-Cpg-Ser-DCpg-DIglb-Arg
12. DArg-Arg-Pro-Hyp-Gly-Cpg-Ser-DTic-Iglb-Arg
13. DArg-Arg-Pro-Hyp-Gly-Cpg-Ser-DTic-DIglb-Arg
14. DArg-Arg-Pro-Hyp-Gly-Phe-Ser-Iglb-Oic-Arg
15. DArg-Arg-Pro-Hyp-Gly-Phe-Ser-DIglb-Oic-Arg
16. DArg-Arg-Pro-Hyp-Gly-Thi-Ser-Nigb-Oic-Arg
17. DArg-Arg-Pro-Hyp-Gly-Iglb-Ser-DTic-Oic-Arg
18. DArg-Arg-Pro-Hyp-Gly-DIglb-Ser-DTic-Oic-Arg
19. DArg-Arg-Pro-Hyp-Gly-Thi-Ser-DIgl-Iglb-Arg
20. DArg-Arg-Pro-Hyp-Gly-Thi-Ser-Cpg-Nigb-Arg
21. DArg-Arg-Pro-Hyp-Gly-Thi-Ser-Iglb-Tic-Arg
22. DArg-Arg-Pro-Hyp-Gly-Thi-Ser-DIglb-Tic-Arg
23. DArg-Arg-Pro-Hyp-Gly-Thi-Ser-DTic-Nigb-Arg
24. DArg-Arg-Pro-Hyp-Gly-Cpg-Ser-DIglb-Oic-Arg
25. DArg-Arg-Pro-Hyp-Gly-Iglb-Ser-DTic-Oic-Arg
26. DArg-Arg-Pro-Hyp-Gly-DMF-Ser-DIglb-Oic-Arg
27. DArg-Arg-Pro-Hyp-Gly-DDMF-Ser-DIglb-Oic-Arg
28. DArg-Arg-Pro-Hyp-Gly-Thi-Ser-DIgl-Nigb-Arg
29. DArg-Arg-Pro-Hyp-Gly-Cpg-Ser-DTic-Nigb-Arg
30. DArg-Arg-Pro-Hyp-Gly-DIglb-Ser-DIglb-Oic-Arg
31. DArg-Arg-Pro-Hyp-Gly-DThi-Ser-DIglb-Oic-Arg
32. DArg-Arg-Pro-Hyp-Gly-Nigb-Ser-DIglb-Oic-Arg
33. DArg-Arg-Pro-Hyp-Nigb-Thi-Ser-DIglb-Oic-Arg
34. DArg-Arg-Pro-Hyp-Gly-Iglb-Ser-DIglb-Cpg-Arg
35. DArg-Arg-Pro-Hyp-Gly-Thi-Ser-DIglb-Leu-Arg
36. DArg-Arg-Pro-Hyp-Gly-Thi-Ser-DIglb-Thi-Arg
37. DArg-Arg-Pro-Hyp-Gly-Thi-Ser-DIglb-AC6-Arg
38. DArg-Arg-Pro-Hyp-Gly-Thi-Ser-DIglb-Ile-Arg
39. DArg-Arg-Pro-Hyp-Gly-Thi-HBQ-DIglb-Oic-Arg
40. DArg-Arg-Pro-Hyp-Gly-Thi-Ser-DIglb-cLeu-Arg
41. DArg-Arg-Pro-Hyp-Gly-Thi-Ser-DIglb-Dic-Arg
42. DArg-Arg-Pro-Hyp-Gly-Thi-Ser-DIglb-Nbn-Arg
43. DArg-Arg-Pro-Hyp-Gly-Iglb-Ser-DTic-Nigb-Arg
44. DArg-Arg-Pro-Hyp-Gly-Iglb-Ser-DIglb-Iglb-Arg
45. DArg-Arg-NMF-Hyp-Gly-Iglb-Ser-DIglb-Oic-Arg
46. DArg-Arg-Pro-Hyp-Gly-Iglb-Ser-DCpg-Cpg-Arg
47. Eac-DArg-Arg-Pro-Hyp-Gly-Thi-Ser-DIglb-Oic-Arg
Suc-DArg-Arg-Pro-Hyp-Gly-Thi-Ser-DIglb-Oic-Arg
48. (SEQ ID NO:5) Aca-DArg-Arg-Pro-Hyp-Gly-Thi-Ser-DTic-Nigb-Arg
49. Aca-DArg-Arg-Pro-Hyp-Gly-Thi-Ser-Nigb-Oic-Arg
50. Dhq-DArg-Arg-Pro-Hyp-Gly-Cpg-Ser-DTic-Iglb-Arg
51. Dhq-DArg-Arg-Pro-Hyp-Gly-Cpg-Ser-DTic-DIglb-Arg
52. (SEQ ID NO:6) Aca-DArg-Arg-Pro-Hyp-Gly-Phe-Ser-Iglb-Oic-Arg
53. Aca-DArg-Arg-Pro-Hyp-Gly-Phe-Ser-DIglb-Oic-Arg
54. Aca-DArg-Arg-Pro-Hyp-Gly-Thi-Ser-Iglb-Oic-Arg
55. Aca-DArg-Arg-Pro-Hyp-Gly-Thi-Ser-DIglb-Oic-Arg
56. Aaa-DArg-Arg-Pro-Hyp-Gly-Thi-Ser-DIglb-Oic-Arg
57. DCha-DArg-Arg-Pro-Hyp-Gly-Thi-Ser-DIglb-Oic-Arg
58. Dcg-DArg-Arg-Pro-Hyp-Gly-Thi-Ser-DIglb-Oic-Arg
59. Dhq-DArg-Arg-Pro-Hyp-Gly-Thi-Ser-DIglb-Oic-Arg
60. Sin-DArg-Arg-Pro-Hyp-Gly-Thi-Ser-DIglb-Oic-Arg
61. Aca-DArg-Arg-Pro-Hyp-Gly-Thi-Ser(SO)-DIglb-Oic-Arg
62. Aca-DArg-Arg-Pro-Hyp-Gly-Iglb-Ser-DTic-Oic-Arg
63. Aaa-DArg-Arg-Pro-Hyp-Gly-Iglb-Ser-DIglb-Oic-Arg
64. Dca-DArg-Arg-Pro-Hyp-Gly-Iglb-Ser-DIglb-Oic-Arg
65. Dpa-DArg-Arg-Pro-Hyp-Gly-Iglb-Ser-DIglb-Oic-Arg
66. Dpp-DArg-Arg-Pro-Hyp-Gly-Iglb-Ser-DIglb-Oic-Arg
67. Nbc-DArg-Arg-Pro-Hyp-Gly-Iglb-Ser-DIglb-Oic-Arg
68. Nbi-DArg-Arg-Pro-Hyp-Gly-Iglb-Ser-DIglb-Oic-Arg
69. Paa-DArg-Arg-Pro-Hyp-Gly-Iglb-Ser-DIglb-Oic-Arg
70. Pba-DArg-Arg-Pro-Hyp-Gly-Iglb-Ser-DIglb-Oic-Arg
71. Ppa-DArg-Arg-Pro-Hyp-Gly-Iglb-Ser-DIglb-Oic-Arg
72. Sin-DArg-Arg-Pro-Hyp-Gly-Iglb-Ser-DIglb-Oic-Arg
73. Aaa-DArg-Arg-Pro-Hyp-Gly-Iglb-Ser-DIglb-Iglb-Arg
74. Aca-DArg-Arg-Pro-Hyp-Gly-Iglb-Ser-DIglb-Iglb-Arg
75. Dca-DArg-Arg-Pro-Hyp-Gly-Iglb-Ser-DIglb-Iglb-Arg
76. Dhq-DArg-Arg-Pro-Hyp-Gly-Iglb-Ser-DIglb-Iglb-Arg
77. Dpa-DArg-Arg-Pro-Hyp-Gly-Iglb-Ser-DIglb-Iglb-Arg
78. Dpp-DArg-Arg-Pro-Hyp-Gly-Iglb-Ser-DIglb-Iglb-Arg
79. Nbc-DArg-Arg-Pro-Hyp-Gly-Iglb-Ser-DIglb-Iglb-Arg
80. Nbi-DArg-Arg-Pro-Hyp-Gly-Iglb-Ser-DIglb-Iglb-Arg
81. Paa-DArg-Arg-Pro-Hyp-Gly-Iglb-Ser-DIglb-Iglb-Arg
82. Pba-DArg-Arg-Pro-Hyp-Gly-Iglb-Ser-DIglb-Iglb-Arg
83. Ppa-DArg-Arg-Pro-Hyp-Gly-Iglb-Ser-DIglb-Iglb-Arg
84. Sin-DArg-Arg-Pro-Hyp-Gly-Iglb-Ser-DIglb-Iglb-Arg
85. DArg-Arg-Pro-Hyp-Gly-Thi-Ser-DIgla-Niga-Arg
86. DArg-Arg-Pro-Hyp-Gly-Thi-Ser-DIgla-Igla-Arg
87. DArg-Arg-Pro-Hyp-Gly-Thi-Ser-DIgla-Tic-Arg
88. DArg-Arg-Pro-Hyp-Gly-Igla-Ser-DTic-Niga-Arg
89. DArg-Arg-Pro-Hyp-Gly-Cpg-Ser-DIgla-Oic-Arg 90. DArg-Arg-Pro-Hyp-Gly-Iglb-Ser-DIgla-Oic-Arg
91. DArg-Arg-Pro-Hyp-Gly-Igla-Ser-DTic-Oic-Arg
92. DArg-Arg-Pro-Hyp-Gly-Thi-Ser-DIgla-Niga-Arg
93. DArg-Arg-Pro-Hyp-Gly-Nigb-Ser-DIgla-Oic-Arg
94. DArg-Arg-Pro-Hyp-Gly-Igla-Ser-DIglb-Cpg-Arg
95. DArg-Arg-Pro-Hyp-Gly-Iglb-Ser-DIglb-Niga-Arg
96. DArg-Arg-Pro-Hyp-Gly-Igla-Ser-DIglb-Thi-Arg
97. DArg-Arg-Pro-Hyp-Gly-Thi-Ser-DIgla-Ile-Arg
98. DArg-Arg-Pro-Hyp-Gly-Igla-Ser-DIgla-Oic-Arg
99. Aaa-DArg-Arg-Pro-Hyp-Gly-Igla-Ser-DIgla-Oic-Arg
100. Aca-DArg-Arg-Pro-Hyp-Gly-Igla-Ser-DIgla-Oic-Arg
101. Dhq-DArg-Arg-Pro-Hyp-Gly-Igla-Ser-DIgla-Oic-Arg
102. Dca-DArg-Arg-Pro-Hyp-Gly-Igla-Ser-DIgla-Oic-Arg
103. Dpa-DArg-Arg-Pro-Hyp-Gly-Igla-Ser-DIgla-Oic-Arg
104. Dpp-DArg-Arg-Pro-Hyp-Gly-Igla-Ser-DIgla-Oic-Arg
105. Nbc-DArg-Arg-Pro-Hyp-Gly-Igla-Ser-DIgla-Oic-Arg
106. Nbi-DArg-Arg-Pro-Hyp-Gly-Igla-Ser-DIgla-Oic-Arg
107. Paa-DArg-Arg-Pro-Hyp-Gly-Igla-Ser-DIgla-Oic-Arg
108. Pba-DArg-Arg-Pro-Hyp-Gly-Igla-Ser-DIgla-Oic-Arg
109. Ppa-DArg-Arg-Pro-Hyp-Gly-Igla-Ser-DIgla-Oic-Arg
110. Sin-DArg-Arg-Pro-Hyp-Gly-Igla-Ser-DIgla-Oic-Arg
111. DArg-Arg-Pro-Hyp-Gly-Igla-Ser-DIgla-Igla-Arg
112. Aaa-DArg-Arg-Pro-Hyp-Gly-Igla-Ser-DIgla-Igla-Arg
113. Aca-DArg-Arg-Pro-Hyp-Gly-Igla-Ser-DIgla-Igla-Arg
114. Dca-DArg-Arg-Pro-Hyp-Gly-Igla-Ser-DIgla-Igla-Arg
115. Dhq-DArg-Arg-Pro-Hyp-Gly-Igla-Ser-DIgla-Igla-Arg
116. Dpa-DArg-Arg-Pro-Hyp-Gly-Igla-Ser-DIgla-Igla-Arg
117. Dpp-DArg-Arg-Pro-Hyp-Gly-Igla-Ser-DIgla-Igla-Arg
118. Nbc-DArg-Arg-Pro-Hyp-Gly-Igla-Ser-DIgla-Igla-Arg
119. Nbi-DArg-Arg-Pro-Hyp-Gly-Igla-Ser-DIgla-Igla-Arg
120. Paa-DArg-Arg-Pro-Hyp-Gly-Igla-Ser-DIgla-Igla-Arg
121. Pba-DArg-Arg-Pro-Hyp-Gly-Igla-Ser-DIgla-Igla-Arg
122. Ppa-DArg-Arg-Pro-Hyp-Gly-Igla-Ser-DIgla-Igla-Arg
123. Sin-DArg-Arg-Pro-Hyp-Gly-Igla-Ser-DIgla-Igla-Arg
124. Aca-DArg-Arg-Pro-Hyp-Gly-Thi-Ser-DHigb-Oic-Arg
125. DArg-Arg-Pro-Hyp-Gly-Thi-Ser-Higb-Oic-Arg
126. DArg-Arg-Pro-Hyp-Gly-Thi-Ser-DHigb-Oic-Arg
127. Arg-Pro-Hyp-Gly-Iglb-Ser-DIglb-Oic-Arg
128. DArg-Arg-Pro-Hyp-Gly-Iglb-Ser-DIglb-Higb-Arg
129. DArg-Arg-Pro-Hyp-Gly-Iglb-Ser-Iglb-Higb-Arg
130. DArg-Arg-Pro-Hyp-Gly-Thi-Ser-DIglb-Higb-Arg
131. DArg-Arg-Pro-Hyp-Gly-Thi-Ser-Iglb-Higb-Arg
132. DArg-Arg-Pro-Hyp-Gly-Thi-Ser-DIglb-Hyp-Arg
133. Aaa-Arg-Pro-Hyp-Gly-Iglb-Ser-DIglb-Oic-Arg
134. Aca-Arg-Pro-Hyp-Gly-Iglb-Ser-DIglb-Oic-Arg
135. Dhq-Arg-Pro-Hyp-Gly-Iglb-Ser-DIglb-Oic-Arg
136. Sin-Arg-Pro-Hyp-Gly-Iglb-Ser-DIglb-Oic-Arg
137. Aaa-Arg-Pro-Hyp-Gly-Thi- Ser-DIglb-Oic-Arg
138. Aca-Arg-Pro-Hyp-Gly-Thi-Ser-DIglb-Oic-Arg
139. Dhq-Arg-Pro-Hyp-Gly-Thi-Ser-DIglb-Oic-Arg
140. Sin-Arg-Pro-Hyp-Gly-Thi-Ser-DIglb-Oic-Arg
141. Gun-DArg-Arg-Pro-Hyp-Gly-Igla-Ser-DIgla-Igla-Arg
142. Gun-DArg-Arg-Pro-Hyp-Gly-Iglb-Ser-DIglb-Oic-Arg
143. Gun-DArg-Arg-Pro-Hyp-Gly-Thi-Ser-DIglb-Oic-Arg
144. Gun-DArg-Arg-Pro-Hyp-Gly-Iglb-Ser-DIglb-Aoc-Arg
145. DArg-Arg-Pro-Hyp-Gly-Iglb-Ser-DIglb-Aoc-Arg
146. DArg-Arg-Pro-Hyp-Gly-Phe-Ser-DIglb-Aoc-Arg
147. DArg-Arg-Pro-Hyp-Gly-Thi-Ser-DIglb-Aoc-Arg
148. DArg-Arg-Pro-Hyp-Gly-Cpg-Ser-DIglb-Aoc-Arg
149. DArg-Arg-Pro-Pro-Gly-Iglb-Ser-DIglb-Iglb-Arg
150. DArg-Arg-Pro-Pro-Gly-Iglb-Ser-DIglb-Oic-Arg
151. DArg-Arg-Pro-Pro-Gly-Iglb-Ser-DIglb-Aoc-Arg
152. Aaa-DArg-Arg-Pro-Hyp-Gly-Iglb-Ser-DIglb-Aoc-Arg
153. Aca-DArg-Arg-Pro-Hyp-Gly-Iglb-Ser-DIglb-Aoc-Arg
154. Dca-DArg-Arg-Pro-Hyp-Gly-Iglb-Ser-DIglb-Aoc-Arg
155. Dhq-DArg-Arg-Pro-Hyp-Gly-Iglb-Ser-DIglb-Aoc-Arg
156. Dpa-DArg-Arg-Pro-Hyp-Gly-Iglb-Ser-DIglb-Aoc-Arg
157. Dpp-DArg-Arg-Pro-Hyp-Gly-Iglb-Ser-DIglb-Aoc-Arg
158. Nbc-DArg-Arg-Pro-Hyp-Gly-Iglb-Ser-DIglb-Aoc-Arg
159. Nbi-DArg-Arg-Pro-Hyp-Gly-Iglb-Ser-DIglb-Aoc-Arg
160. Paa-DArg-Arg-Pro-Hyp-Gly-Iglb-Ser-DIglb-Aoc-Arg
161. Pba-DArg-Arg-Pro-Hyp-Gly-Iglb-Ser-DIglb-Aoc-Arg
162. Ppa-DArg-Arg-Pro-Hyp-Gly-Iglb-Ser-DIglb-Aoc-Arg
163. Sin-DArg-Arg-Pro-Hyp-Gly-Iglb-Ser-DIglb-Aoc-Arg
164. Gun-Arg-Pro-Hyp-Gly-Iglb-Ser-DIglb-Oic-Arg
165. Gun-DArg-Arg-Pro-Hyp-Gly-Thi-Ser-DIglb-Oic-Arg
166. DArg-Arg-Pro-Hyp-Gly-Iglb-Ser-DIglb-Ica-Arg
167. DArg-Arg-Pro-Hyp-Gly-Thi-Ser-DIglb-Pip-Arg 168. DArg-Arg-Pro-Hyp-Gly-Iglb-Ser-DNal-Oic-Arg
169. DArg-Arg-Pro-Hyp-Gly-Thi-Ser-DIglb-DMTP-Arg
170. (SEQ ID NO:7) DArg-Arg-Pro-Hyp-Gly-Iglb-Lys-DIglb-Oic-Arg
171. DArg-Arg-Pro-Hyp-Gly-Iglb-Ser-DIglb-Chg-Arg
172. Arg-Pro-Hyp-Gly-Iglb-Ser-DIglb-Oic-Arg
173. (SEQ ID NO:8) DArg-Arg-Pro-Hyp-Gly-Thi-Ser-DIglb-Tyr-Arg
174. DArg-Arg-Pro-Hyp-Gly-Iglb-Thr-DIglb-Oic-Arg
175. DArg-Arg-Pro-Hyp-Gly-Thi-Glu-DIglb-Oic-Arg
176. (SEQ ID NO:9) DArg-Arg-Pro-Hyp-Gly-His-Ser-DIglb-Oic-Arg
177. (SEQ ID NO:10) Arg-Arg-Pro-Hyp-Gly-Iglb-Ser-DIglb-Oic-Arg
178. DArg-Arg-Pro-Hyp-Gly-Thi-Ser-DIglb-Trp-Arg
179. DArg-Arg-Pro-Hyp-Gly-TMF-Ser-DIglb-Oic-Arg
180. DArg-Arg-Pro-Hyp-Gly-Iglb-Ser-DIglb-MPIV-Arg
181. DArg-Arg-Pro-Hyp-Gly-DMF-Ser-DIglb-Oic-Arg
182. DArg-Arg-Pro-Hyp-Gly-Thi-Ser-DIglb-DMF-Arg
183. DArg-Arg-Pro-Hyp-Gly-Iglb-Ser-DTic-Oic-Arg
184. DArg-Arg-Pro-Hyp-Gly-Iglb-Ser-DAlg-Igl-Arg
185. DArg-Arg-Pro-Hyp-Gly-Iglb-Ser-DTic-Nia-Arg
186. DArg-Arg-Pro-Hyp-Gly-Thi-Ser-DIglb-Nia-Arg
187. DArg-Arg-Pro-Hyp-Gly-Iglb-Ser-DIglb-MEF-Arg
188. DArg-Arg-Pro-Hyp-Gly-Thi-Ser-DIglb-MEF-Arg
189. DArg-Arg-Pro-Hyp-Gly-Thi-Ser-DIglb-TMF-Arg
190. DArg-Arg-Pro-Hyp-Gly-Iglb-Ser-DIglb-TMF-Arg
191. DArg-Arg-Pro-Hyp-Gly-Iglb-Ser-DIglb-Alg-Arg
192. DArg-Arg-Pro-Hyp-Gly-Iglb-Ser-DIglb-Mag-Arg
193. DArg-Arg-Pro-Hyp-Gly-Igl-Ser-DMag-Igl-Arg
194. DArg-Arg-Pro-Hyp-Gly-Iglb-Ser-DMag-Oic-Arg
195. DArg-Arg-Pro-Pro-Gly-Iglb-Ser-DMag-Aoc-Arg
196. Gun-DArg-Arg-Pro-Hyp-Gly-cAcp-Ser-DIglb-Oic-Arg
197. Gun-DArg-Arg-Pro-Hyp-Gly-Iglb-Ser-DIglb-Ica-Arg
198. Gun-DArg-Arg-Pro-Hyp-Gly-Thi-Ser-DIglb-Pip-Arg
199. Gun-DArg-Arg-Pro-Hyp-Gly-Iglb-Ser-DNal-Oic-Arg
200. Gun-DArg-Arg-Pro-Hyp-Gly-Thi-Ser-DIglb-DMTP-Arg
201. (SEQ ID NO:11) Gun-DArg-Arg-Pro-Hyp-Gly-Iglb-Lys-DIglb-Oic-Arg
202. Gun-DArg-Arg-Pro-Hyp-Gly-Iglb-Ser-DIglb-Chg-Arg
203. Gun-Arg-Pro-Hyp-Gly-Iglb-Ser-DIglb-Oic-Arg
204. Gun-DArg-Arg-Pro-Hyp-Gly-Thi-Ser-DIglb-Tyr-Arg
205. (SEQ ID NO:12) Gun-DArg-Arg-Pro-Hyp-Gly-Iglb-Thr-DIglb-Oic-Arg
206. (SEQ ID NO:13) Gun-DArg-Arg-Pro-Hyp-Gly-Thi-Glu-DIglb-Oic-Arg
207. (SEQ ID NO:14) Gun-DArg-Arg-Pro-Hyp-Gly-His-Ser-DIglb-Oic-Arg
208. (SEQ ID NO:15) Gun-Arg-Arg-Pro-Hyp-Gly-Iglb-Ser-DIglb-Oic-Arg
209. (SEQ ID NO:16) Gun-DArg-Arg-Pro-Hyp-Gly-Thi-Ser-DIglb-Trp-Arg
210. Gun-DArg-Arg-Pro-Hyp-Gly-TMF-Ser-DIglb-Oic-Arg
211. Gun-DArg-Arg-Pro-Hyp-Gly-Iglb-Ser-DIglb-MPIV-Arg
212. Gun-DArg-Arg-Pro-Hyp-Gly-DMF-Ser-DIglb-Oic-Arg
213. Gun-DArg-Arg-Pro-Hyp-Gly-Thi-Ser-DIglb-DMF-Arg
214. Gun-DArg-Arg-Pro-Hyp-Gly-Iglb-Ser-DTic-Oic-Arg
215. Gun-DArg-Arg-Pro-Hyp-Gly-Iglb-Ser-DAlg-Igl-Arg
216. Gun-DArg-Arg-Pro-Hyp-Gly-Iglb-Ser-DTic-Nia-Arg
217. Gun-DArg-Arg-Pro-Hyp-Gly-Thi-Ser-DIglb-Nia-Arg
218. Gun-DArg-Arg-Pro-Hyp-Gly-Iglb-Ser-DIglb-MEF-Arg
219. Gun-DArg-Arg-Pro-Hyp-Gly-Thi-Ser-DIglb-MEF-Arg
220. Gun-DArg-Arg-Pro-Hyp-Gly-Thi-Ser-DIglb-TMF-Arg
221. Gun-DArg-Arg-Pro-Hyp-Gly-Iglb-Ser-DIglb-TMF-Arg
222. Gun-DArg-Arg-Pro-Hyp-Gly-Iglb-Ser-DIglb-Alg-Arg
223. Gun-DArg-Arg-Pro-Hyp-Gly-Iglb-Ser-DIglb-Mag-Arg
224. Gun-DArg-Arg-Pro-Hyp-Gly-Igl-Ser-DMag-Igl-Arg
225. Gun-DArg-Arg-Pro-Hyp-Gly-Iglb-Ser-DMag-Oic-Arg
226. Gun-DArg-Arg-Pro-Pro-Gly-Iglb-Ser-DMag-Aoc-Arg
227. Dcg-Arg-Pro-Hyp-Gly-Iglb-Ser-DIglb-Oic-Arg
228. Dcg-DArg-Arg-Pro-Hyp-Gly-cAcp-Ser-DIglb-Oic-Arg
229. Dcg-DArg-Arg-Pro-Hyp-Gly-Iglb-Ser-DIglb-Ica-Arg
230. Dcg-DArg-Arg-Pro-Hyp-Gly-Thi-Ser-DIglb-Pip-Arg
231. Dcg-DArg-Arg-Pro-Hyp-Gly-Iglb-Ser-DNal-Oic-Arg
232. Dcg-DArg-Arg-Pro-Hyp-Gly-Thi-Ser-DIglb-DMTP-Arg
233. (SEQ ID NO:17) Dcg-DArg-Arg-Pro-Hyp-Gly-Iglb-Lys-DIglb-Oic-Arg
234. Dcg-DArg-Arg-Pro-Hyp-Gly-Iglb-Ser-DIglb-Chg-Arg
235. Dcg-Arg-Pro-Hyp-Gly-Iglb-Ser-DIglb-Oic-Arg
236. Dcg-DArg-Arg-Pro-Hyp-Gly-Thi-Ser-DIglb-Tyr-Arg
237. Dcg-DArg-Arg-Pro-Hyp-Gly-Iglb-Thr-DIglb-Oic-Arg
238. Dcg-DArg-Arg-Pro-Hyp-Gly-Thi-Glu-DIglb-Oic-Arg
239. Dcg-DArg-Arg-Pro-Hyp-Gly-His-Ser-DIglb-Oic-Arg
240. (SEQ ID NO:18) Dcg-Arg-Arg-Pro-Hyp-Gly-Iglb-Ser-DIglb-Oic-Arg
241. Dcg-DArg-Arg-Pro-Hyp-Gly-Thi-Ser-DIglb-Trp-Arg 242. Dcg-DArg-Arg-Pro-Hyp-Gly-TMF-Ser-DIglb-Oic-Arg 243. Dcg-DArg-Arg-Pro-Hyp-Gly-Iglb-Ser-DIglb-MPIV-Arg 244. Dcg-DArg-Arg-Pro-Hyp-Gly-DMF-Ser-DIglb-Oic-Arg 245. Dcg-DArg-Arg-Pro-Hyp-Gly-Thi-Ser-DIglb-DMF-Arg 246. Dcg-DArg-Arg-Pro-Hyp-Gly-Iglb-Ser-DTic-Oic-Arg 247. Dcg-DArg-Arg-Pro-Hyp-Gly-Iglb-Ser-DAlg-Igl-Arg 248. Dcg-DArg-Arg-Pro-Hyp-Gly-Iglb-Ser-DTic-Nia-Arg 249. Dcg-DArg-Arg-Pro-Hyp-Gly-Thi-Ser-DIglb-Nia-Arg 250. Dcg-DArg-Arg-Pro-Hyp-Gly-Iglb-Ser-DIglb-MEF-Arg 251. Dcg-DArg-Arg-Pro-Hyp-Gly-Thi-Ser-DIglb-MEF-Arg 252. Dcg-DArg-Arg-Pro-Hyp-Gly-Thi-Ser-DIglb-TMF-Arg 253. Dcg-DArg-Arg-Pro-Hyp-Gly-Iglb-Ser-DIglb-TMF-Arg 254. Dcg-DArg-Arg-Pro-Hyp-Gly-Iglb-Ser-DIglb-Alg-Arg 255. Dcg-DArg-Arg-Pro-Hyp-Gly-Iglb-Ser-DIglb-Mag-Arg 256. Dcg-DArg-Arg-Pro-Hyp-Gly-Igl-Ser-DMag-Igl-Arg 257. Dcg-DArg-Arg-Pro-Hyp-Gly-Iglb-Ser-DMag-Oic-Arg 258. Dcg-DArg-Arg-Pro-Pro-Gly-Iglb-Ser-DMag-Aoc-Arg 259. Dcg-DArg-Arg-Pro-Hyp-Gly-Iglb-Ser-DIglb-Oic-Arg 260. DArg-Arg-Pro-Hyp-Gly-cAcp-Ser-DIglb-Oic-Arg 261. Bpg-DArg-Arg-Pro-Hyp-Gly-cAcp-Ser-DIglb-Oic-Arg 262. Bpg-DArg-Arg-Pro-Hyp-Gly-Iglb-Ser-DIglb-Ica-Arg 263. Bpg-DArg-Arg-Pro-Hyp-Gly-Thi-Ser-DIglb-Pip-Arg 264. Bpg-DArg-Arg-Pro-Hyp-Gly-Iglb-Ser-DNal-Oic-Arg 265. Bpg-DArg-Arg-Pro-Hyp-Gly-Thi-Ser-DIglb-DMTP-Arg 266. Bpg-DArg-Arg-Pro-Hyp-Gly-Iglb-Lys-DIglb-Oic-Arg 267. Bpg-DArg-Arg-Pro-Hyp-Gly-Iglb-Ser-DIglb-Chg-Arg 268. Bpg-Arg-Pro-Hyp-Gly-Iglb-Ser-DIglb-Oic-Arg 269. (SEQ ID NO:19) Bpg-DArg-Arg-Pro-Hyp-Gly-Thi-Ser-DIglb-Tyr-Arg 270. Bpg-DArg-Arg-Pro-Hyp-Gly-Iglb-Thr-DIglb-Oic-Arg 271. Bpg-DArg-Arg-Pro-Hyp-Gly-Thi-Glu-DIglb-Oic-Arg 272. Bpg-DArg-Arg-Pro-Hyp-Gly-His-Ser-DIglb-Oic-Arg 273. Bpg-Arg-Arg-Pro-Hyp-Gly-Iglb-Ser-DIglb-Oic-Arg 274. Bpg-DArg-Arg-Pro-Hyp-Gly-Thi-Ser-DIglb-Trp-Arg 275. Bpg-DArg-Arg-Pro-Hyp-Gly-TMF-Ser-DIglb-Oic-Arg 276. Bpg-DArg-Arg-Pro-Hyp-Gly-Iglb-Ser-DIglb-MPIV-Arg 277. Bpg-DArg-Arg-Pro-Hyp-Gly-DMF-Ser-DIglb-Oic-Arg 278. Bpg-DArg-Arg-Pro-Hyp-Gly-Thi-Ser-DIglb-DMF-Arg 279. Bpg-DArg-Arg-Pro-Hyp-Gly-Iglb-Ser-DTic-Oic-Arg 280. Bpg-DArg-Arg-Pro-Hyp-Gly-Iglb-Ser-DAlg-Igl-Arg 281. Bpg-DArg-Arg-Pro-Hyp-Gly-Iglb-Ser-DTic-Nia-Arg 282. Bpg-DArg-Arg-Pro-Hyp-Gly-Thi-Ser-DIglb-Nia-Arg 283. Bpg-DArg-Arg-Pro-Hyp-Gly-Iglb-Ser-DIglb-MEF-Arg 284. Bpg-DArg-Arg-Pro-Hyp-Gly-Thi-Ser-DIglb-MEF-Arg 285. Bpg-DArg-Arg-Pro-Hyp-Gly-Thi-Ser-DIglb-TMF-Arg 286. Bpg-DArg-Arg-Pro-Hyp-Gly-Iglb-Ser-DIglb-TMF-Arg 287. Bpg-DArg-Arg-Pro-Hyp-Gly-Iglb-Ser-DIglb-Alg-Arg 288. Bpg-DArg-Arg-Pro-Hyp-Gly-Iglb-Ser-DIglb-Mag-Arg 289. Bpg-DArg-Arg-Pro-Hyp-Gly-Igl-Ser-DMag-Igl-Arg 290. Bpg-DArg-Arg-Pro-Hyp-Gly-Iglb-Ser-DMag-Oic-Arg 281. Bpg-DArg-Arg-Pro-Pro-Gly-Iglb-Ser-DMag-Aoc-Arg 292. Bpg-DArg-Arg-Pro-Hyp-Gly-Iglb-Ser-DIglb-Oic-Arg 293. Bpg-DArg-Arg-Pro-Hyp-Gly-Thi-Ser-DIglb-Oic-Arg (Compound 47 represents a dimeric compound).

Example XI

Biological Activity

The bradykinin antagonists were assayed on isolated rat uterus in natural or induced estrus and on guinea pig ileum, according to the commonly accepted assay methods for bradykinin and related kinins as described by Trautschold (Handbook of Experimental Pharmacology, Vol. 25, Springer-Verlag, pp 53–55, (1969)) for inhibition of the myotropic activity of bradykinin. The inhibition potencies were determined according to the commonly accepted manner, as described by Schild for antagonists of biologically active compounds (*Brit. J. Pharmacol.* 2: 189 (1947)) and expressed as $pA_2$ values. In the assays, a dose-response curve was determined for the reference substance bradykinin. The dose of bradykinin which produces a half-maximal contraction of the tissue is the $ED_{50}$ dose. An amount of bradykinin equivalent to twice the $ED_{50}$ dose was administered to the tissue 30 seconds after the start of incubation of the tissue with a dose of antagonist. Doses of antagonist were increased in this protocol until the dose of antagonist was found that caused the tissue response to a double $ED_{50}$ dose of bradykinin in the presence of antagonist to equal the response of an $ED_{50}$ dose of bradykinin without antagonist.

The $pA_2$ value, therefore, represents the negative logarithm of the molar concentration of antagonist necessary to reduce the response to a double $ED_{50}$ dose of bradykinin to that of an $ED_{50}$ dose without antagonist. A change of one unit of $pA_2$ value represents an order of magnitude change in potency. For comparison, the negative logarithm of the dose of bradykinin that causes half-maximal contraction of the tissues, commonly known as the $pD_2$ value, is 7.9 on the rat uterus and 7.4 on the guinea pig ileum.

The in vivo effects of bradykinin antagonists on blood pressure in the anesthetized rat were determined according to the assay described by Roblero, Ryan and Stewart (*Res. Commun. Pathol. Pharmacol.* 6: 207 (1973)). The antagonists produce inhibition of the hypotensive action of bradykinin when administered as a bolus admixture of bradykinin plus antagonist or when administered as an infusion. Potencies for the antagonists in this assay are not reported precisely, but rather are indicated approximately.

On isolated smooth muscles, agonist potency is given as percent of BK potency; antagonist potency is given as $pA_2$, and is underlined. In blood pressure assays, the number is the dose of peptide in micrograms that causes 50% reduction in the effect of BK intraarterially administered as a bolus mixture in a 500 g male rat; Ag indicates unquantitated agonist activity; Ant indicates unquantitated antagonist activity.

TABLE I

Biological Activities of Typical Peptide Examples

| Compound Number | Uterus Activity | Ileum Activity | Blood Pressure |
|---|---|---|---|
| 1. | 8.5 | 7.9 | 0.5 |
| 2. | 7.5 | 7.8 | 5 |
| 3. | 7.4 | 7.6 | 5 |
| 5. | | 7.7 | |
| 7. | 7.8 | 7.4 | 5 |
| 9. | 7.4 | 7.2 | 5 |
| 12. | 10.5% | 5.1 | 0 |
| 13. | 8.6% | 6.0 | 0 |
| 14. | 6.5 | 5.1 | 0 |
| 15. | 7.9 | 7.6 | 0.05 |
| 16. | 6.8 | 7.0 | 0.5 |
| 17. | Ant | Ant | 5 |
| 18. | | | 5 |
| 19. | 9.1% | 6.7 | Ag |
| 22. | 7.0 | 6.8 | 0.5 |
| 23. | 8.3 | 7.2 | 0.5 |
| 24. | | 8.1 | 5 |
| 25. | 0.7% | 7.8 | 0.5 |
| 26. | 7.3 | 6.6 | 5 |
| 27. | 8.0 | 6.9 | 0.5 |
| 28. | 48.6% | 6.5 | 0.05 |
| 29. | 8.1 | 7.6 | 5 |
| 30. | 8.0 | 7.8 | 0.5 |
| 31. | 8.2 | 6.0 | 5 |
| 32. | | 5.3 | |
| 33. | 5.0 | 5.1 | |
| 34. | 7.8 | 6.8 | 0.05 |
| 35. | 3.3% | 6.8 | |
| 36. | 3.0% | 5.4 | 50 |
| 37. | 7.0 | 6.0 | |
| 38. | | 6.8 | 0.5 |
| 39. | 7.1 | | 5 |
| 40. | | | 5 |
| 41. | | | 50 |
| 43. | | | 0.5 |
| 44. | | | 50 |
| 45. | | 6.5 | 0.5 |
| 48. | 6.0 | | |
| 49. | 7.1 | 6.5 | 50 |
| 50. | | 5.4 | 5 |
| 51. | 0.3% | 5.8 | 50 |

TABLE I-continued

Biological Activities of Typical Peptide Examples

| Compound Number | Uterus Activity | Ileum Activity | Blood Pressure |
|---|---|---|---|
| 52. | 7.2 | 5.9 | 0 |
| 53. | 8.2 | 7.4 | 0.5 |
| 54. | 5.8 | | |
| 55. | 9.2 | 8.4 | 0.5 |
| 56. | 7.7 | 7.8 | 5 |
| 58. | 3.0% | 5.4 | |
| 59. | 8.1 | 7.2 | 0.5 |
| 60. | 8.3 | 7.3 | 0.05 |
| 61. | | 7.5 | 0.5 |
| 124. | | 7.7 | 0 |
| 125. | 9.4% | 6.6 | Ag |

Example XII

Human Ileum

Human ilea were obtained from a human tissue bank (International Institute for the Advancement of Medicine, Exton, Pa). Sections 25 mm×5 mm were placed under 2gm isometric resting tension in 4 ml tissue baths containing Krebs-Henseleit solution and bubbled with 95% $O_2$ and 5% $CO_2$. Concentration-effect curves were constructed to BK in the absence and presence of different doses of antagonist. The antagonist potency ($pA_2$, i.e. the negative log of the concentration of the antagonist which produced a 2-fold shift in the concentration-effect curve to bradykinin) was calculated using the method of Schild (1947).

| Compound | Human Ileum B2 receptor | n |
|---|---|---|
| 1 | 8.75 ± 0.08 | 7 |
| 7 | 7.79 ± 0.18 | 13 |

Example XIII

B1 Receptor Bioassay

Male New Zealand white rabbits, weight range 2–3 kg, were killed by an overdose of pentobarbital i.v. The thorax was opened and the thoracic aorta carefully removed. Spiral strips, approximately 25×3–4 mm were prepared and placed in 4 ml tissue baths containing Krebs solution at 37° C. and bubbled with 95% $O_2$ and 5% $CO_2$. The tissues were placed under 1 gm isometric tension and allowed to equilibrate for 1H. At time 1h, a concentration-effect curve was constructed to the selective B1 agonist des-$Arg^9$-BK. This was repeated at time 3 hours. At time 5h des-$Arg^9$-BK was added to the tissue bath at a final concentration of $10^{-7}$ M. This produced a sustained contraction that could be maintained for approximately 45 min. Once the contraction was sustained, the compound to be assayed was applied to the tissue bath in a cumulative manner. The concentration of the compound which produced a 50% reduction of the sustained contraction was calculated. The negative logarithm of this concentration was calculated and expressed as the $IC_{50}$. All compounds were compared to the standard B1 antagonist des-$Arg^{10}$-$Leu^9$-kallidin which had a $pIC_{50}$ of 7.9.

| Compound | Rabbit Aorta p IC50 B1 receptors | n |
|---|---|---|
| 1 | 6.60 ± 0.03 | 4 |
| 2 | 5.75 ± 0.23 | 5 |
| 3 | 5.93 ± 0.17 | 5 |
| 5 | 5.81 ± 0.19 | 5 |
| 7 | 6.85 ± 0.21 | 6 |
| 11 | 6.4 ± 0.03 | 3 |
| 15 | 6.79 ± 0.27 | 3 |
| 22 | 5.75 ± 0.03 | 8 |
| 23 | <5 | 5 |
| 24 | 6.37 ± 0.08 | 8 |
| 25 | 5.32 ± 0.06 | 6 |
| 27 | <5 | 3 |
| 28 | <5 | 4 |
| 30 | <5 | 3 |
| 31 | <5 | 3 |
| 45 | 5.54 ± 0.08 | 6 |
| 47 | 5.35 ± 0.18 | 4 |
| 53 | 5.9 ± 0.10 | 2 |
| 55 | 6.57 ± 0.21 | 6 |
| 56 | 6.16 ± 0.29 | 2 |
| 60 | 5.68 ± 0.13 | 6 |
| 61 | 5.38 ± 0.08 | 4 |

Example XIV

Human B2 Binding

Human B2 receptors were cloned and expressed in Chinese hamster ovary cells. RNA was isolated from human lung fibroblasts (CCD-16 LU obtained from the ATCC) using the method of Chirgwin et al (*Biochemistry* 18:5294 (1979)). The RNA was transcribed into cDNA using MMLV reverse transcriptase, the primer GACTCGAGTCGA-CATCGATTTTTTTTTTTTTTTTTT and the procedure of Maniatis (Molecular Cloning Cold Spring Harbor Laboratory (1982)). The human B2 receptor cDNA was selectively amplified using nested PCR. The first round PCR used the two primers CTCCGAGGAGGGGTGGG and CCT-GAAAAGCAACTGTCCC and Taq DNA polymerase (Promega). Twenty-five rounds of PCR were done using the following conditions: 94° C., 1 minute for denaturation, 50° C., 1 minute for annealing followed by 72° C., 3 minutes for extension. Excess primers were removed with a Centricon 30 miniconcentrator. A portion of this first round reaction was used as a template in a second round of PCR using the following primers GCGAAGCTTCGTGAGGACTCCGT-GCCC and CGCTCTAGACAAATTCACAGCCC. The number of rounds of PCR and the conditions were the same as those used for the first round. The DNA obtained after this second round was digested with the restriction enzymes Hind III and Xba I using standard methodology. Cesium chloride-purified pRc/CMV (Invitrogen) was also digested with Hind III and Xba I using standard methodology. The products of the two digests were resolved on a 1% low melt agarose gel. The human B2 receptor DNA (approximately 1.1 kb) and the pRc/CMV DNA (approximately 5.5 kb) were excised from the gel. The gel slices containing these DNAs were heated at 65° C. and aliquots combined in a reaction containing T4 DNA ligase. The reaction was incubated overnight at 15° C.

An aliquot of this reaction was used to transform frozen competent *E. coli* DH5α cells (GibcoBRL). Transformants containing the human B2 receptor DNA were selected on LB+amp plates. One of the transformants was selected and the sequence of the human B2 receptor DNA insert determined using the Sequenase enzyme (United States Biochemical) according to the manufacturer's instructions. This sequence was compared to the sequence of Hess et al (*Biochemical and Biophysical Research Communications* 184:260 1992)). Several nucleotide misincorporations were detected and those that altered the amino acid sequence of the receptor were corrected using site-directed mutagenesis (Kunkel et al *Methods in Enzymology* 154:367 (1987)). The human BK2 receptor-pRc/CMV plasmid was transfected into CHO-k1 cells using the Lipofectamine reagent (GibcoBRL). Transfectants were selected with the antibiotic G418 and screened for $^3$H-bradykinin (Dupont NEN) binding. One clone, S34f, was chosen based upon binding levels, binding kinetics and inhibition patterns as the clone to be used for all human B2 receptor binding assays.

Cells containing the receptor were grown to confluence and harvested by scraping into PBS and homogenized. Membranes were prepared by centrifugation in 25 mM TES pH6.8 containing 1 mM 1.10 Phenanthroline. The final pellet was resuspended in assay buffer (25 mM TES, 1 mM 1.10 Phenanthroline, 1 mM DTT, 2M Captopril, 0.1% BSA pH=6.8) and frozen. In binding experiments, 60 μg membranes were incubated in 315 μl of assay buffer with 0.3 nM 3H-Bradykinin and various amounts of test compound. Incubation was carried out at room temperature for 45 min. The assay was terminated by filtration through a polyethylenimine soaked G-A filter. Radioactivity was measured on a Wallac 1450 MicroBeta LSC.

The $K_d$ for the receptor was determined by kinetic analysis of on and off rates utilizing a single exponential decay off rate. $K_i$'s for compounds were calculated using the following equation: $K_i=IC_{50}/(1+[L]/K_d)$, where L=free ligand concentration. For comparison, the Ki for bradykinin was 10.4±0.3.

| Compound | Human Receptor Clone B2 receptor binding | n |
|---|---|---|
| 1 | 15.2 | 1 |
| 2 | 10.35 | 2 |
| 3 | 11.85 | 2 |
| 5 | 10.16 | 2 |
| 7 | 14.1 | 1 |
| 15 | 13.95 | 2 |
| 16 | 9.51 | 2 |
| 22 | 10.9 | 2 |
| 23 | 10.8 | 3 |
| 24 | 12.25 | 3 |
| 25 | 12.9 | 1 |
| 27 | 9.75 | 2 |
| 28 | 12.83 | 2 |
| 30 | 12.2 | 2 |
| 31 | 11 | 2 |
| 45 | 9.85 | 2 |
| 47 | 10.26 | 2 |
| 53 | 10.85 | 2 |
| 56 | 9.4 | 2 |
| 60 | 10.16 | 2 |
| 61 | 8.39 | 2 |

Example XV

Dog Blood Pressure

Mongrel dogs of either sex, weight range 10–15 kg were used. These were anaesthetized with pentobarbital, 30 mg/kg i.v., and catheters were placed in one femoral artery and both femoral veins for the recording of blood pressure and infusion and injection of compounds. Responses to BK (1 nM) and des-Arg$^9$-BK (50 nM) were produced in the absence and presence of antagonist as described above for the rabbit, and the $ED_{50}$ was calculated. After the end of the infusion of the highest dose of compound 1 or 7 (1μg/kg/min), BK and des-$Arg_9$-BK were injected at intervals for up to four hours.

| | BLOOD PRESSURE DATA | |
|---|---|---|
| Compound | Dog B2 | B1 |
| 1 | 0.03 | 0.24 |
| 7 | 0.17 | 0.35 |

Mean $ED_{50}$ values in mg/kg/min for compounds 1 and 7 against B2 and B1 receptors-mediated hypotensive responses in the dog. (n=3).

Duration of action: For the dog, following a 25 minute infusion of 1 mg/kg/min of compound 7 responses to BK and des-$Arg^9$-Bk were normal 60 minutes later. On the other hand, after compound 1, responses to both kinins were still 100% blocked at 4 hours.

What is claimed is:

1. A bradykinin antagonist of the formula $$X\text{-}A^0\text{-}B^1\text{-}C^2\text{-}D^3\text{-}E^4\text{-}F^5\text{-}G^6\text{-}H^7\text{-}J^8\text{-}K^9$$

wherein

X is absent or is Dcg, Sin, Dca, Dpp, Nbc, Nbi, Paa, Pba, Ppa, Bpg, Aaa, Aca, Acetyl, Dhq, Nba, Tba, Cha, Gun, or Cpa;

$A^0$ s DArg, DLys, Arg, Lys, Aaa, Gun, Dcg, Bpg or is absent;

$B^1$ is DArg, DLys, Arg or Lys;

$C^2$ is Pro, DMF, NMF, MPIV, Hyp, Azt, Dhp, Inip, Thz, or Pop;

$D^3$ is Hyp, Pop, Niga, MPIV, Pro, Azt, Dhp, Inip, or Thz;

$E^4$ is Gly, Iglb, Nigb, Ala, or Gly;

$F^5$ is Ser (SO), Leu, Chg, Ile, Val, Alg, Oic, Pop, Nle, Phe, Thi, Cpg or DMF;

$G^6$ is Ser, HBQ, Cys, or Gly;

$H^7$ is DLeu, DChg, DIle, DVal, DCpg, DOic, DPop, DNle, DTic or DDMF;

$J^8$ is Igla, Lys, Niga, Nigb, Leu, Chg, Ile, Val, Cpg, Oic, Pop, Tic, Nbn, or Nle; and $K^9$ is Arg or DArg; provided that at least one of $F^5$, $H^7$ or $J^8$ is D- or L-Igla, Iglb, Niga or Nigb.

2. The bradykinin antagonist according to claim 1, wherein $F^5$ is Phe, Thi, Cpg, or Chg.

3. The bradykinin antagonist according to claim 1, wherein $H^7$ is D-Tic, D-Cpg, or D-Chg.

4. The bradykinin antagonist according to claim 1, wherein $J^8$ is Tic, Nbn, Oic, Cpg, or Chg.

5. The bradykinin antagonist according to claim 1, wherein $A^0$ is D-Arg;

$B^1$ is Arg;

$C^2$ is Pro or Hyp;

$D^3$ is Pro or Hyp;

$E^4$ is Gly;

$G^6$ is Ser, Ser(SO), or HBQ; and $K^9$ is Arg.

6. The bradykinin antagonist according to claim 1, of the formula

H-DArg-Arg-Pro-Hyp-Gly-Iglb-Ser-DIglb-Iglb-Arg.

7. According to claim 1, of the formula

DArg-Arg-Pro-Hyp-Gly-Iglb-Ser-DIglb-Oic-Arg

DArg-Arg-Pro-Hyp-Gly-Thi-Ser-DIglb-Oic-Arg.

Gun-Arg-Pro-Hyp-Gly-Iglb-Ser-DIglb-Oic-Arg or

Gun-Arg-Pro-Hyp-Gly-Thi-Ser-DIglb-Oic-Arg.

8. A method of treating or preventing pain or inflammation caused by overproduction of bradykinin administering to a host in need of such treatment an efffective amount of the compound according to claim 1 with a pharmaceutically acceptable carrier.

9. A method of treating premature labor in a patient in need of such treatment comprising administering an amount of a compound of claim 1 effective to reduce contractions caused by overproduction of bradykinin.

10. The compound:

Eac-DArg-Arg-Pro-Hyp-Gly-Thi-Ser-DIglb-Oic-Arg |
Suc-DArg-Arg-Pro-Hyp-Gly-Thi-Ser-DIglb-Oic-Arg.

* * * * *